United States Patent [19]

Hasegawa et al.

[11] Patent Number: 4,933,282

[45] Date of Patent: Jun. 12, 1990

[54] PROCESS FOR PREPARING AN OPTICALLY ACTIVE GAMMA-HALO-BETA-HYDROXYBUTYRIC ACID ESTER

[75] Inventors: Masayasu Hasegawa, Kyoto; Shigetaka Okada, Ikoma; Nobutake Hamada, Nara; Kiyofumi Sakai, Osaka; You Honda, Hirakata, all of Japan

[73] Assignee: Nippon Gohsei Kagaku Kogyo Kabushiki Kaisha, Osaka, Japan

[21] Appl. No.: 935,199

[22] Filed: Nov. 26, 1986

[30] Foreign Application Priority Data

Nov. 28, 1985 [JP] Japan ................................. 60-268811

[51] Int. Cl.$^5$ .......................... C12P 7/62; C12P 41/00; C12N 1/18
[52] U.S. Cl. .................................... 435/135; 435/280; 435/244; 435/254; 435/255
[58] Field of Search ............... 435/280, 244, 135, 171, 435/940, 942, 254, 255

[56] References Cited

FOREIGN PATENT DOCUMENTS 2132614 7/1984 United Kingdom .

OTHER PUBLICATIONS

ATCC Catalog of Fungi, 1987, pp. 346–347.

Primary Examiner—Charles F. Warren
Assistant Examiner—Irene Marx
Attorney, Agent, or Firm—Antonelli, Terry, Stout & Kraus

[57] ABSTRACT

A process for preparing an optically active γ-halo-β-hydroxybutyric acid ester in high yields which comprises subjecting a γ-haloacetoacetic acid ester to the action of a microorganism selected from genus Saccharomyces under an anaerobic condition. When the γ-haloacetoacetic acid ester is subjected to the action of the microorganism in the presence of a ketal, the yield and optical purity can be further increased.

3 Claims, No Drawings

PROCESS FOR PREPARING AN OPTICALLY ACTIVE γ-HALO-β-HYDROXYBUTYRIC ACID ESTER

BACKGROUND OF THE INVENTION

The present invention relates to a process for preparing an optically active γ-halo-β-hydroxybutyric acid ester by microbiologically treating a γ-hyloacetoacetic acid ester.

In case of preparing a γ-halo-β-hydroxybutyric acid ester by chemically reducing a γ-haloacetoacetic acid ester, a yield of desired products is low because dehalogenation occurs easily.

On the other hand, side reactions such as dehalogenation do not occur in a process for microbiologically reducing a γ-haloacetoacetic acid ester. There is known a process for microbiologically preparing a γ-halo-β-hydroxybutyric acid ester by employing a baker's yeast under an aerobic condition. But the process gives only a low yield of the desired products, which is not practical on an industrial scale.

SUMMARY OF THE INVENTION

In accordance with the present invention, there is provided a process for preparing an optically active γ-halo-β-hydroxybutyric acid ester which comprises subjecting a γ-haloacetoacetic acid ester to the action of a microorganism selected from genus Saccharomyces under an anaerobic condition. According to the present invention, the γ-halo-β-hydroxybutyric acid can be prepared in high yields.

DETAILED DESCRIPTION

The γ-haloacetoacetic acid esters used in the invention as a starting material is a compound obtained by reacting a diketene with a halogen in an organic solvent and has the following formula:

X—CH$_2$CO.CH$_2$COOR wherein X is a halogen atom, R is an organic residue.

Among halogen atoms X, chlorine atom and bromine atom are practical. The group R can be any of preferable organic residues having about 1 to about 20 carbon atoms, such as an alkyl group, an aralkyl group, an aryl group. Representative examples of the γ-haloacetoacetic acid ester used in the present invention are γ-chloro-acetoacetic acid methyl ester, γ-choloroacetoacetic acid ethyl ester, γ-bromoacetoacetic acid octyl ester, γ-chloroacetoacetic acid benzyl ester and γ-bromoacetoacetic acid methyl ester.

Representative examples of the microorganisms used in the invention are, for example, *Sacchromyces cerevisiae* [IFO 0250], *Saccharomyces logos* [IFO 1225], *Saccharomyces carlsbergensis* [IFO 0565], *Saccharomyces bisporus* [IFO 0467], *Saccharomyces chevalieri* [IFO 0333], *Saccharomyces delbrueckii* [IFO 0955], *Saccharomyces fermentati* [IFO 0422], *Saccharomyces globosus* [IFO 0752], *Saccharomyces montanus* [IFO 0851] *Saccharomyces rosei* [IFO 0431] and *Saccharomyces rouxii* [IFO 0934]. [IFO 0431] and *Saccharomuces rouxii* [IFO 0439]. These microorganisms are available to anybody at the Institute for Fermentation, Osaka (IFO).

There are many kinds of medium for the employed strain. For example; YM medium of pH 5.5 containing 3 g of yeast extract, 3 g of malt extract, 5 g of peptone, 10 g glucose and 1 l of water, YP meduim of pH 5.5 containing 3 g of yeast extract, 3 g of peptone, 20 g of glucose, 100 mg of chloramphenicol and 1 l of water, Sabouraud's medium of pH 6.0 containing 10 g of peptone, 40 g of glucose and 1 l of water and blackstrap molasses medium of pH 5.5 containing 20 g of molasses, 1.65 g of ammonium sulfate, 0.22 g of potassium primary phosphate and 1 l of water.

Moreover, the above media can be used as an agar plate medium by adding 15 g of agar to each medium. Further, proper amount of vitamin or mineral can be added to the above media.

In case of using a liquid culture medium, a conventional manner of aerobic culture is taken under conditions of the temperature range from 25° to 35° C. pH range from 4 to 5 and dissolved oxygen amount range from 1 to 2 ppm. Defoaming agent can be added to the liquid culture medium. The culture period is 20 to 60 hours.

It is characteristic in the invention that the reaction of the γ-halo-β-hydroxybutyric acid ester with a microorganism is carried out under the anaerobic condition. The yield of the desired products is improved enormously be using this condition.

The expression "anaerobic condition" as used herein means a state of substantial absence of oxygen, in other words, under an atmosphere of an inert gas such as nitrogen, carbon dioxide, argon gas or helium gas, under an atmosphere of hydrogen gas or under reduced pressure condition that oxygen is removed from an ordinary atmospheric condition.

In the reactions a microorganism is dispersed into an aqueous system such as water, physiological saline, buffer solution, culture medium, or the like, by adding sugar group as the energy. Then a γ-haloacetoacetic acid ester is added and shaken or stirred, under the temperature range from 10° to 70° C. (preferably from 20° to 40° C.) and the time from 0.1 to 150 hours (preferably from 0.5 to 7 hours) and also the pH range from 3 to 9 (preferably from 4 to 7.5).

Another method, such as reacting this ester with the immobilized microorganism, is also useful. The adoptable reaction system is either a batch method or a continuous method by flowing a γ-haloacetoacetic acid ester through the pipe or tower where the immobilized microoganism is filled up.

The preferable solvents are not only water but also mixture of water and organic solvent having a compatibility with water, such as alcohol or acetone, which are harmless against the microoganism The γ-haloacetoacetic acid ester is added to the reaction system either directly or in the form of solution or dispersion of the organic solvent.

The adoptable concentration of this ester is usually from 0.01 to 50% by weight, preferably 0.05 to 20% by weight.

Moreover, the useful ratio of this ester and the microoganism by weight (dry weight) is 1:1 or less, preferably 1:0.01 to 0.8.

Sugar group such as glucose or a stroma of a microorganism may be added during the reaction.

The sugar group or stroma is added to the system at any step of the reaction and in any manner, for example, supplied at once, intermittently or continuously. The yield is advanced when the sugar group is added in the amount of 5 to 100% by weight against the dry weight of the microorganism.

Further, when the γ-haloacetoacetic acid ester is subjected to the microbiological reduction in the presence of a ketal as represented by the formula:

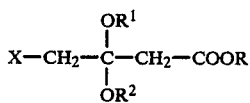

the yield and optical purity can be increased. Wherein X is H or a halogen atom, and R, $R^1$ and $R^2$ can be any of organic residues such as an alkyl, aralkyl and aryl group having 1 to 10 carbon atoms. The amount of the ketal is from 0.1 to 5 times, preferably from 0.4 to 2.0 times weight of the γ-haloacetoacetic acid ester.

When the reaction is over, the microorganism is separated by the centrifuge and then the supernatant is extracted by the organic solvent such as ether, carbon tetrachloride or benzene.

A γ-halo-β-hydroxybutyric acid ester is obtained by evaporating the organic solvent from the extraction solution.

According to this present invention, an optically active γ-halo-α-hydroxybutyric acid ester is obtained in such a high yield as over 80%.

The process in the present invention is industrially useful and also this obtained ester is useful as an intermediate of drugs such as carnitine and γ-amino-β-hydroxybutyric acid.

The present invention is more specifically described and explained by means of the following Examples. It is to be understood that the present invention is not limited to the Examples, and various changes and modifications may be in the invention without departing from the spirit and scope thereof.

EXAMPLE 1

*Saccharomyces cerevisiae* [IFO 0250] was subjected to shaking culture for 48 hours in YM medium (3 g yeast extract, 3 g of malt extract, 5 g of peptone, 10 g of glucose, 1 l of water, pH 5.5) and cells were collected and washed to give viable microbe cells.

Fifty milliliters of deionized water was added to a 500 ml Sakaguchi's flask and the previous viable microbe cells (4 g by dry weight) was suspended. After adding 0.8 g of glucose and successsively 1 g of ethyl γ-chloracetoacetate to the cell suspension, the flask was displaced with nitrogen gas, that is, the dissolved oxygen was displaced with nitrogen gas by bubbling nitrogen gas through the cell suspension for 30 minutes at the rate of 3.0 l per minute at 20° C., and the flask was closed, and was shaken reciprocally for 3 hours at 27° C.

After the completion of the reaction, the reaction mixture free from microorganisms was extracted with 50 ml of ethyl acetate. Anhydrous magnesium sulfate was added to the dehydrated ethyl acetate layer and then the ethyl acetate was evaporated from the layer.

By means of IR and NMR, the residue of extract was identified as ethyl γ-chloro-β-hydroxybutyrate. IR spectrum and NMR spectrum of the obtained product are shown below:

| $IR_{cm^{-1}}^{on\ KBr}$: 3460 (OH), 1730 (C = O) NMR (solvent: CDCl₃, Standard: TMS): | |
|---|---|
| δ values (ppm) | Assignment (underline) |
| 1.3 (t) | —C—O—CH₂.CH₃ (with C=O) |
| 2.6 (d) | —CH—CH₂—C—O— (OH on CH, C=O) |
| 3.6 (d) | Cl—CH₂—CH— (OH) |
| 4.2 (q) | —C—O—CH₂.CH₃ (C=O) |
| 4.2 (m) | Cl—CH₂—CH—CH₂ (OH) |

The yield of 95% by mole was estimated by means of high pressure liquid chromatography.

The specific rotation of this ester was $[\alpha]^{23}$ +20.5 (5.7% by weight of chloroform solution).

When the same reaction of Example 1 was carried out under an aerobic condition, without replacement with nitrogen gas, that is, in the open Sakaguchi's flask, the yield of ethyl γ-chlor-β-hydroxybutyrate was only 75%.

EXAMPLES 2 to 11

By using the microorganisms (4 g by dry weight) shown in Table 1, a γ-halo-β-hydroxybutyric acid ester was prepared by the same procedure as in Example 1. The γ-halo-β-hydroxybutyric acid ester was identified by means of IR and NMR.

The results are shown in Table 1, involving the data of the yield under the aerobic condition as a reference.

TABLE 1

| | | | | | | Yield of produced γ-halo-β-hydroxybutyric acid ester (%) | |
|---|---|---|---|---|---|---|---|
| | | γ-haloacetoacetic acid esters | | Glucose | Kind of | Under anaerobic condition | Under aerobic condition |
| Ex. No. | Microorganism | Kind | Amount (g) | (g) | ester | | |
| 2 | Saccharomyces cerevisiae (IFO 0250) | Octyl γ-bromo-acetoacetate | 2 | 0.7 | Octyl | 90 | 64 |
| 3 | | | 2 | 3.5 | | 83 | 60 |
| 4 | | Benzyl γ-chloro-acetoacetate | 0.5 | 0 | Benzyl | 96 | 72 |
| 5 | | | 2 | 1 | | 88 | 60 |
| 6 | Saccharomyces | Methyl γ-bromo- | 0.2 | 0.5 | Methyl | 98 | 77 |

TABLE 1-continued

| Ex. No. | Microorganism | γ-haloacetoacetic acid esters Kind | Amount (g) | Glucose (g) | Kind of ester | Yield of produced γ-halo-β-hydroxybutyric acid ester (%) Under anaerobic condition | Under aerobic condition |
|---|---|---|---|---|---|---|---|
| 7 | | acetoacetate | 2 | 0.5 | | 87 | 61 |
| 8 | logos (IFO 1225) | Allyl γ-chloro- | 3 | 0.5 | Allyl | 82 | 58 |
| 9 | | acetoacetate | 4 | 0.5 | | 80 | 52 |
| 10 | Saccharomyces carlsbergensis (IFO 0565) | Ethyl γ-chloro- | 1 | 0.8 | Ethyl | 98 | 78 |
| 11 | | acetoacetate | 2 | 1 | | 85 | 63 |

EXAMPLE 12

*Saccharomyces rouxii* [IFO 0439] was cultured for 20 hours in a blackstrap molasses medium (20 g of blackstrap molasses, 1.65 g of ammonium sulfate, 0.22 g of potassium primary phosphate, 1 l of water, pH 5.5) in a jar-fermenter, and cells were collected and washed to give viable microbe cells.

Twenty four milliliters of suspension of microbe cells was made by adding the previous viable mcirobe cell (5.2 g by dry weight) and deionized water into a 500 ml Sakaguchi's flask.

After adding 1 g of glucose, 4 g of octyl γ-chloroacetoacetate and 3 g of a ketal having the formula:

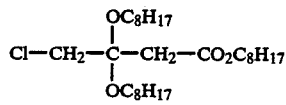

the flask was displaced with carbon dioxide. The flask was closed and was shaken reciprocally for 3 hours at 27° C.

After the completion of the reaction, the reaction mixture reactant free from microoganisms was extracted with 80 ml of hexane. Anhydrous magnesium sulfate was added to the dehydrated hexane layer and then hexane was evaporated from the layer.

The residue of extract was purified by a silica-gel chromatography (solvent: toluene/ether=4/1), thus oily octyl γ-chloro-β-hydroxybutyrate was obtained (yield 98%). The octyl γ-chloro-β-hydroxy-butyrate was identified by means of IR and NMR.

The specific rotation of this ester was $[\alpha]_D^{20}$ +14.7 (5.0% by weight chloroform solution).

The same reaction as above was conducted under an aerobic condition, without replacement with carbon dioxide. The yield of octyl γ-chloro-β-hydroxybutyrate was only 61% and the specific rotation was $[\alpha]_D^{20}$ +13.0 (5.0% by weight chloroform solution).

EXAMPLES 13 to 28

By using the microorganisms (5.2 g by dry weight) shown in Table 2, a γ-halo-β-hydroxybutyric acid ester was prepared by the same procedure as in Example 12. The γ-halo-β-hydroxybutyric acid ester was identified by means of IR and NMR.

The results are shown in Table 2, involving the data of the yield under the aerobic condition.

In addition to the ingredients used in the Examples as set forth in the specification to obtain substantially the same results.

TABLE 2

| Ex. No. | Microorganism | γ-haloacetoacetic acid esters Kind | Amount (g) | Ketal Kind (shown below) | Amount (g) | Glucose (g) | Kind of ester | Yield of produced γ-halo-β-hydroxybutyric acid ester (%) Under anaerobic condition | Under aerobic condition |
|---|---|---|---|---|---|---|---|---|---|
| 13 | Saccharomyces rouxii [IFO 0439] | Pentyl γ-bromo- | 3 | A* | 3 | 1 | Pentyl | 95 | 60 |
| 14 | | acetoacetate | 5 | C* | 2 | 1 | | 93 | 58 |
| 15 | | Allyl γ-chloro- | 4 | B* | 4 | 1 | Allyl | 85 | 52 |
| 16 | | acetoacetate | 2 | A* | 4 | 0.8 | | 90 | 55 |
| 17 | Saccharomyces cerevisiae [IFO 0250] | Octyl γ-chloro- | 4 | A* | 3 | 1 | Octyl | 98 | 65 |
| 18 | | acetoacetate | 4 | A* | 0 | 1 | | 90 | 60 |
| 19 | | Methyl γ-bromo- | 5 | A* | 2 | 0.7 | Methyl | 95 | 65 |
| 20 | | acetoacetate | 6 | A* | 7 | 0.9 | | 93 | 70 |
| 21 | Saccharomyces delbrueckii [IFO 0955] | Butyl γ-chloro- | 2 | A* | 3 | 1 | Butyl | 92 | 61 |
| 22 | | acetoacetate | 3 | B* | 4 | 0.7 | | 92 | 61 |
| 23 | | Ethyl γ-chloro- | 5 | A* | 4 | 1 | Ethyl | 95 | 72 |
| 24 | | acetoacetate | 5 | A* | 0 | 1 | | 90 | 60 |
| 25 | | Octyl γ-chloro- | 1 | B* | 1 | 1.5 | | 88 | 54 |

TABLE 2-continued

| Ex. No. | Microorganism | γ-haloacetoacetic acid esters Kind | Amount (g) | Ketal Kind (shown below) | Amount (g) | Glucose (g) | Kind of ester | Yield of produced γ-halo-β-hydroxybutyric acid ester (%) Under anaerobic condition | Under aerobic condition |
|---|---|---|---|---|---|---|---|---|---|
| 26 | *Saccharomyces rosei* [IFO 0431] | acetoacetate | 2 | C* | 2 | 1.2 | Octyl | 86 | 58 |
| 27 | | t-butyl-γ-bromo- | 6 | C* | 7 | 1 | t-butyl | 92* | 65 |
| 28 | | acetoacetate | 3 | A* | 1 | 1 | | 90 | 60 |

Notes:

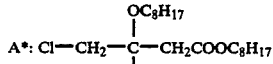

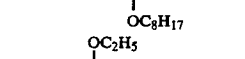

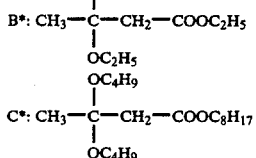

What we claim is;

1. A process for preparing an optically active γ-halo-β-hydroxybutyric acid ester of the formula (I):

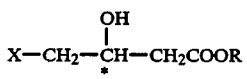

wherein X is a halogen atom, and R is an alkyl group having 1 to 20 carbon atoms, a benzyl group or an allyl group, which comprises subjecting a γ-haloacetoacetic acid ester of the formula (II):

wherein X and R are as defined above to the action of *Saccharomyces cerecisiae* [IFO 0250] under an anaerobic condition.

2. The process of claim 1, wherein said γ-haloacetoacetic acid ester is subjected to the action of a microorganism in the presence of ketal of the formula (III):

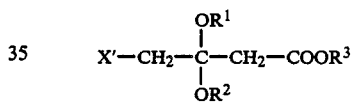

wherein X' is H or a halogen atom, and $R^1$, $R^2$ and $R^3$ are same or different and represent an alkyl group having 1 to 10 carbon atoms, a benzyl group or an allyl group.

3. The process of claim 2, wherein said ketal is used in an amount of 0.1 to 5 times the weight of said γ-haloacetoacetic acid ester.

UNITED STATES PATENT AND TRADEMARK OFFICE
CERTIFICATE OF CORRECTION

PATENT NO. : 4,933,282
DATED : June 12, 1990
INVENTOR(S) : Masayasu HASEGAWA et al.

It is certified that error appears in the above-identified patent and that said Letters Patent is hereby corrected as shown below:

On the Title Page:

Item [73] - The Assignee information should correctly read as follows:

--Nippon Gohsei Kagaku Kogyo Kabushiki Kaisha, Osaka, Japan and Osaka Municipal Government, Osaka, Japan--

Signed and Sealed this

Third Day of September, 1991

*Attest:*

HARRY F. MANBECK, JR.

*Attesting Officer*     *Commissioner of Patents and Trademarks*